(12) United States Patent
Lee et al.

(10) Patent No.: US 11,981,760 B2
(45) Date of Patent: May 14, 2024

(54) THERAPEUTIC HYDROGELS AND CONTACT LENS FOR CORNEAL MELTING

(71) Applicants: THE REGENTS OF THE UNIVERSITY OF COLORADO, Denver, CO (US); UNIVERSITY OF NEW HAMPSHIRE, Durham, NH (US)

(72) Inventors: Jung-Jae Lee, Aurora, CO (US); Kyung Jae Jeong, Durham, NH (US)

(73) Assignees: The Regents of the University of Colorado, a body corporate, Denver, CO (US); University of New Hampshire, Durham, NH (US)

( * ) Notice: Subject to any disclaimer, the term of this patent is extended or adjusted under 35 U.S.C. 154(b) by 626 days.

(21) Appl. No.: 17/256,354

(22) PCT Filed: Jun. 28, 2019

(86) PCT No.: PCT/US2019/039916
§ 371 (c)(1),
(2) Date: Dec. 28, 2020

(87) PCT Pub. No.: WO2020/006471
PCT Pub. Date: Jan. 2, 2020

(65) Prior Publication Data
US 2021/0261701 A1     Aug. 26, 2021

Related U.S. Application Data

(60) Provisional application No. 62/691,774, filed on Jun. 29, 2018.

(51) Int. Cl.
| | |
|---|---|
| *C08F 20/40* | (2006.01) |
| *A61K 9/00* | (2006.01) |
| *A61P 27/02* | (2006.01) |
| *C07D 213/38* | (2006.01) |
| *C08J 3/075* | (2006.01) |

(52) U.S. Cl.
CPC ............ *C08F 20/40* (2013.01); *A61K 9/0051* (2013.01); *A61P 27/02* (2018.01); *C07D 213/38* (2013.01); *C08J 3/075* (2013.01); *C08J 2333/14* (2013.01)

(58) Field of Classification Search
CPC ........ C08F 20/40; A61P 27/02; A61K 9/0051; C07D 213/38; C08J 3/075; C08J 2333/14
See application file for complete search history.

(56) References Cited

U.S. PATENT DOCUMENTS

| | | |
|---|---|---|
| 2017/0043017 A1 | 2/2017 | Obata et al. |
| 2017/0119811 A1 | 5/2017 | Klein et al. |

FOREIGN PATENT DOCUMENTS

| | | | |
|---|---|---|---|
| EP | 3329910 A1 | | 6/2018 |
| JP | 2012097211 A | * | 5/2012 |
| WO | 2014092958 A1 | | 6/2014 |

OTHER PUBLICATIONS

International Search Report and Written Opinion dated Sep. 10, 2019 for International Application No. PCT/US19/39916.
Buruiana, et al., "Copolymers based on N-acryloyl-L-leucine and urea methacrylate with pyridine moieties", J Serb Chem Soc, vol. 81, No. 3, 2016, pp. 307-322.
Lopez, et al., "Matrix Metalloproteinase-Deactivating Contact Lens for Corneal Melting", ACS Biomater. Sci. Eng., 5, 2019, 1195-1199.
Rietsch, et al., "ExsE, a secreted regulator of type III secretion genes in Pseudomonas aeruginosa", PNAS, vol. 102, No. 22, May 31, 2005, pp. 8006-8011.
Wabmann, et al., "Influence of quaternization of ammonium on antibacterial activity and cytocompatibility of thin copolymer layers on titanium", J Biomater Sci, Polymer Edition, vol. 27, No. 15, 2016, pp. 1507-1519.

* cited by examiner

*Primary Examiner* — Alma Pipic
(74) *Attorney, Agent, or Firm* — Saul Ewing LLP; Domingos J. Silva; Alireza Behrooz

(57) ABSTRACT

The present invention relates to the unexpected discovery of a cross-linked polymer of 2-hydroxyethyl methacrylate and dipicolylamine-containing monomers that can be used as a therapeutic lens to treat ocular diseases or disorders associated with matrix metalloproteinase (MMP) over-activity and/or over-expression, such as but not limited to corneal melting (or keratolysis).

17 Claims, 11 Drawing Sheets a) 2-chloroethanol, toluene, reflux, 6h, 90 %
b) methacryloyl chloride, diethyl ether, 0 °C, 4h, quant.

or a) NaBH(OAc)$_3$, AcOH, THF, rt, 3 days, 71 % b) methacryloyl chloride, diethyl ether, 0 °C, 4h, 95 %

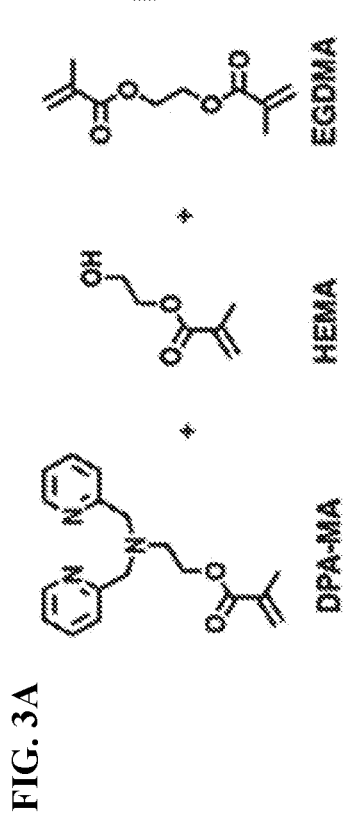
FIG. 3A
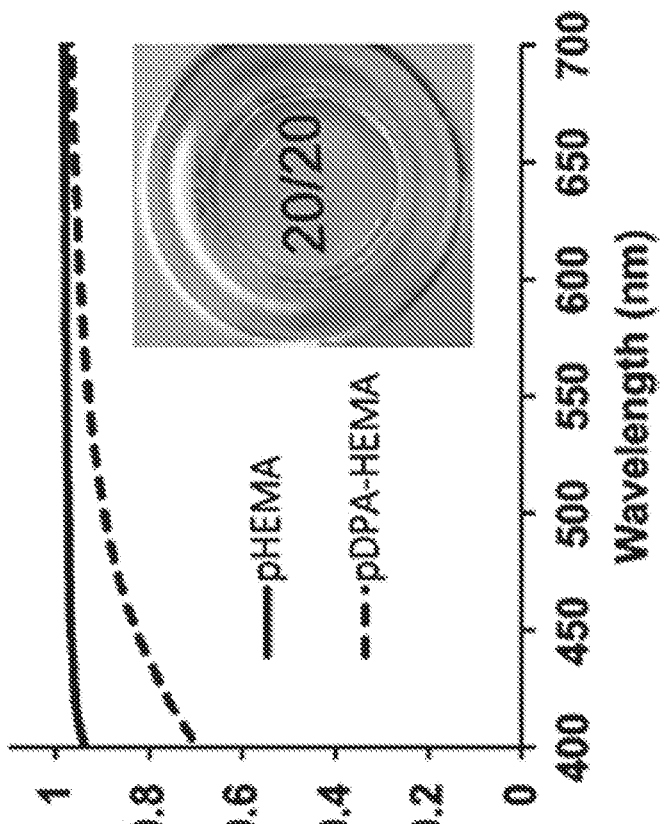
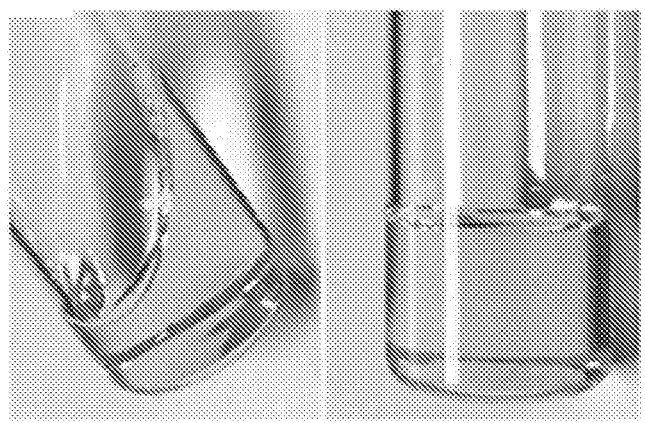
FIG. 3B
FIG. 3C

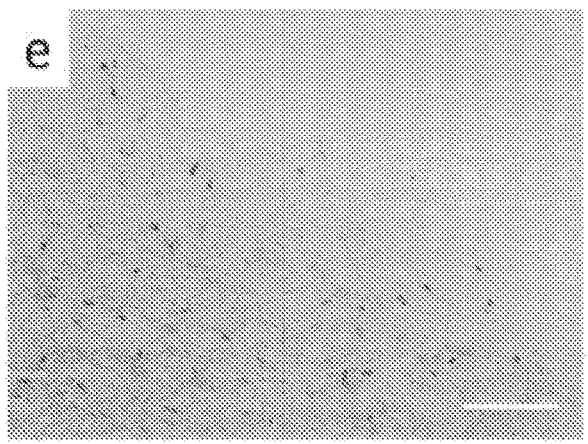 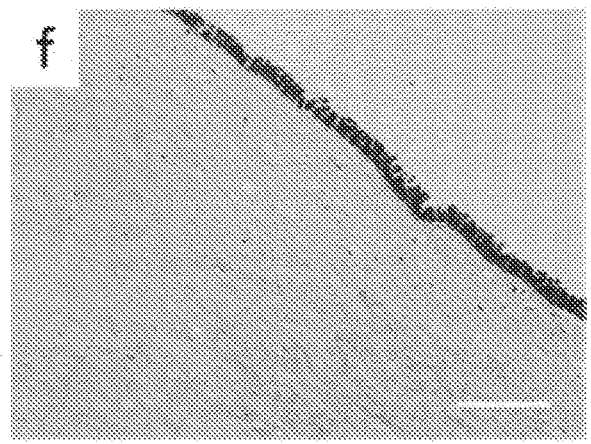
FIG. 5E  FIG. 5F
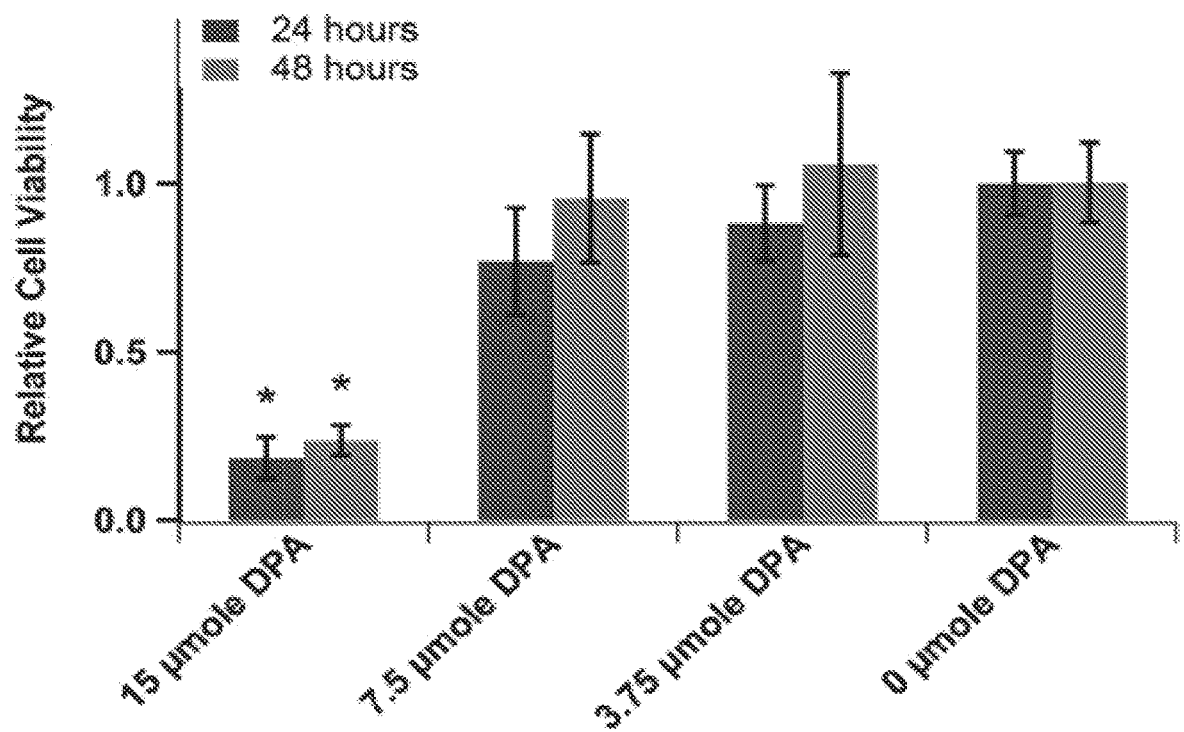
FIG. 6 pDPA-HEMA pDPA-py-HEMA a) 4-toluenesulfonyl chloride, pyridine, 0 °C b) 2,6-pyridinediethanol, $K_2CO_3$, ACN, reflux
c) methacryloyl chloride, diethyl ether, 0 °C

THERAPEUTIC HYDROGELS AND CONTACT LENS FOR CORNEAL MELTING

CROSS-REFERENCE TO RELATED APPLICATIONS

The present application is a 35 U.S.C. § 371 national phase application from, and claims priority to, PCT International Patent Application No. PCT/US2019/039916, filed Jun. 28, 2019, which claims priority under 35 U.S.C. § 119(e) to U.S. Provisional Application No. 62/691,774, filed Jun. 29, 2018, all of which are hereby incorporated by reference herein in their entireties.

STATEMENT REGARDING FEDERALLY SPONSORED RESEARCH OR DEVELOPMENT

This invention was made with government support under grant number EY027953 awarded by National Institutes of Health. The government has certain rights in the invention.

BACKGROUND OF THE INVENTION

Corneal melting, which corresponds to an uncontrolled excessive degradation of corneal tissue, is associated with various ocular diseases, such as ulcerative keratitis and autoimmune diseases (e.g., Stevens-Johnson Syndrome and rheumatoid arthritis). Ocular surgical procedures, such as cataract, glaucoma and LASIK surgeries, affecting millions of patients each year, significantly increase the risk of corneal melting. In addition, chemical burns to the cornea, affecting 30,000 workers annually in the U.S., often progress to corneal melting. When treated improperly, corneal melting results in cornea failure and can lead to eventual vision loss. Current treatment methods for corneal melting include topical application of steroidal anti-inflammatory drugs, application of tissue adhesives or amniotic membrane transplantation, and corneal transplantation. To date, however, there is no satisfying cure to this eye condition.

The tear film of patients who had corneal melting comprises an abnormally high accumulation of matrix metalloproteinases (MMPs). MMPs are zinc-dependent enzymes with zinc-binding sites within the enzymatic domain. The zinc ion in MMPs assists the cleavage of collagens by polarizing the scissile peptide bond, enabling nucleophilic attack of a catalytic solvent molecule. Most zinc ions in the human body are bound to albumin, which also has a binding site for zinc. MMPs are essential proteins for the renewal of extracellular matrices (ECMs) of tissues, and abnormal regulation of MMP production has been implicated in various diseases, including cancer metastasis. Although the detailed profiles of elevated MMPs depend on the etiology of corneal melting, use of MMP inhibitors (MMPi) could be used as therapeutic agents, as the MMPi deactivates MMPs by binding to the zinc binding domains of MMPs. However, systemic circulation of the MMPi is nearly impossible to avoid, and can cause serious side effects due to indiscriminate inhibition of essential MMPs located outside the eye environment.

There is thus a need in the art for compositions and methods that can be used to treat or prevent corneal melting in a subject in need thereof. The present invention addresses this unmet need in the art.

BRIEF SUMMARY OF THE INVENTION

In one aspect, the invention provides a polymer comprising 2-hydroxyethyl methacrylate (HEMA) monomers and at least one dipicolylamine (DPA)-containing methacrylate monomer. In another aspect, the invention provides a method of treating keratolysis in an eye of a subject, the method comprising applying to the eye of the subject a contact lens comprising the polymer as described elsewhere herein.

In certain embodiments, the polymer depletes the corneal tissue and/or tear film of an eye of a subject from $Zn^{2+}$ ion. In certain embodiments, the polymer is not substantially cytotoxic to the eye of the subject.

BRIEF DESCRIPTION OF THE DRAWINGS

The following detailed description of selected embodiments of the invention will be better understood when read in conjunction with the appended drawings. For the purpose of illustrating the invention, specific embodiments are illustrated in the drawings. It should be understood, however, that the invention is not limited to the precise arrangements and instrumentalities of the embodiments illustrated in the drawings.

FIG. 1A is a general schematic illustrating deactivation of MMPs by the pDPA-HEMA based contact lens. FIG. 1B is a schematic illustrating deactivation of MMP-9 by the pDPA-HEMA based contact lens by selectively sequestering $Zn^{2+}$ ions over other cations.

FIGS. 3A-3C illustrate synthesis and characterization of pDPA-HEMA. FIG. 3A show photopolymerization of pDPA-HEMA: DPAs are conjugated to the polymeric network of HEMA cross-linked byEGDMA. FIG. 3B are photographs of pDPA-HEMA (5% of DPA with HEMA) before (top) and after (bottom) UV irradiation for 1 h; the resulting hydrogel was transparent with a slight yellow tint. FIG. 3C is a graph showing transmittance spectrum of pHEMA and pDPA-HEMA hydrogels.

FIG. 4A is a graph depicting results from zinc assay illustrating the specific zinc-absorbing capacity of pDPA-HEMA hydrogel in the absence and presence of calcium: hydrogels (8 mm in diameter, 2 mm in thickness) were immersed in 1.0 mL of 1.0 mM $ZnCl_2$ or 1.0 mL of 1.0 mM $ZnCl_2$ and 10 mM $CaCl_2$ for 1 h, and the amount of zinc ions remaining in the solution was measured using a fluorescent indicator for zinc. 3.75 and 7.5 μmol of DPA in the pHEMA hydrogel correspond to 2.5 and 5% DPA. FIGS. 4B-4C are SEM images of small pieces of pDPA-HEMA (FIG. 4B) and pHEMA hydrogels (FIG. 4C) after the zinc absorption study (the graphs in FIG. 4B and FIG. 4C represent the amount of zinc obtained by EDS along the dashed lines). FIGS. 4D-4E show zinc elemental mapping of pDPA-HEMA and pHEMA hydrogels after the zinc absorption study; the bright pixels represent Zn (scale bar=100 μm).

FIGS. 5A-5F illustrate effects of pDPA-HEMA hydrogels on MMPs. FIG. 5A is a bar graph illustrating deactivation of MMPs by pHEMA and pDPA-HEMA hydrogels. x-axis indicates the amount of DPA in the pHEMA hydrogel; 7.5 and 15 μmol of DPA correspond to 5 and 10% DPA in the hydrogel, respectively. FIG. 5B is a bar graph illustrating ex vivo degradation of porcine cornea: the time it takes for the complete degradation of porcine cornea was measured. * and ** denote $p<0.05$ and $p<0.01$, respectively (n=4). DPA concentration was 10% for pDPA-HEMA. FIGS. 5C-5F are optical micrographs of H&E stained histology sections: untreated cornea and corneas incubated in 0.15% collagenase A solution for 8 h (FIG. 5C), without any hydrogel (FIG. 5D), with pHEMA hydrogel (FIG. 5E), and with pDPAHEMA hydrogel. Scale bar=200 μm (FIG. 5D).

FIG. 6 is a bar graph illustrating in vitro cytotoxicity of pDPA-HEMA on HCECs.

DETAILED DESCRIPTION OF THE INVENTION

The present invention relates to the unexpected discovery that a cross-linked polymer of 2-hydroxyethyl methacrylate (HEMA) monomers and dipicolylamine (DPA)-containing monomers can be used as therapeutic lens to treat ocular diseases or disorders associated with MMP over-activity and/or over-expression. Non-limiting examples of such diseases or disorders include corneal melting (or keratolysis), which is an uncontrolled, excessive degradation of cellular and extracellular components of the cornea. This potential cause of corneal blindness is known to be caused by excessive expression of zinc-dependent matrix metalloproteinases (MMPs) and has no satisfying cure as of now.

Figure 1A:
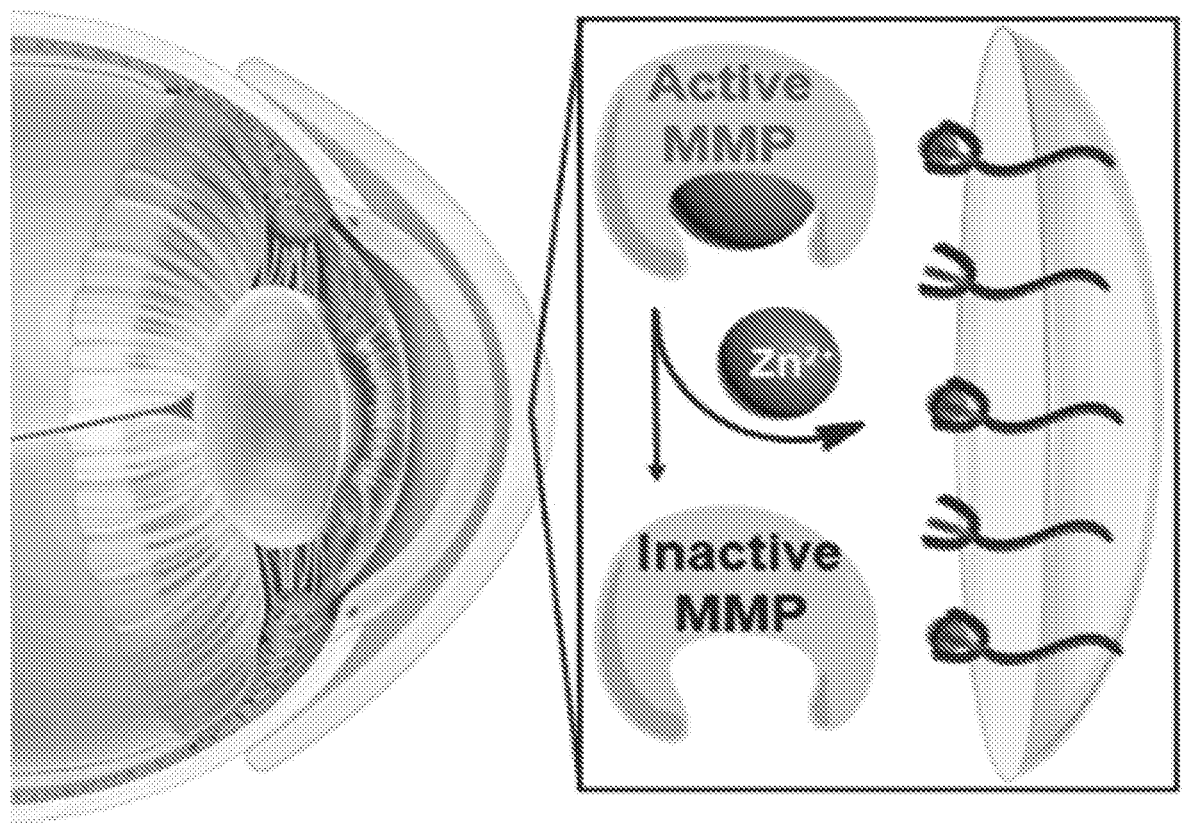
FIGS. 1A-1B illustrate that a pDPA-HEMA-based contact lens selectively absorbs zinc ions in the tear film and induces loss of zinc ions from MMPs, which are thus deactivated, leading to reduction in corneal melting.
Figure 1B:
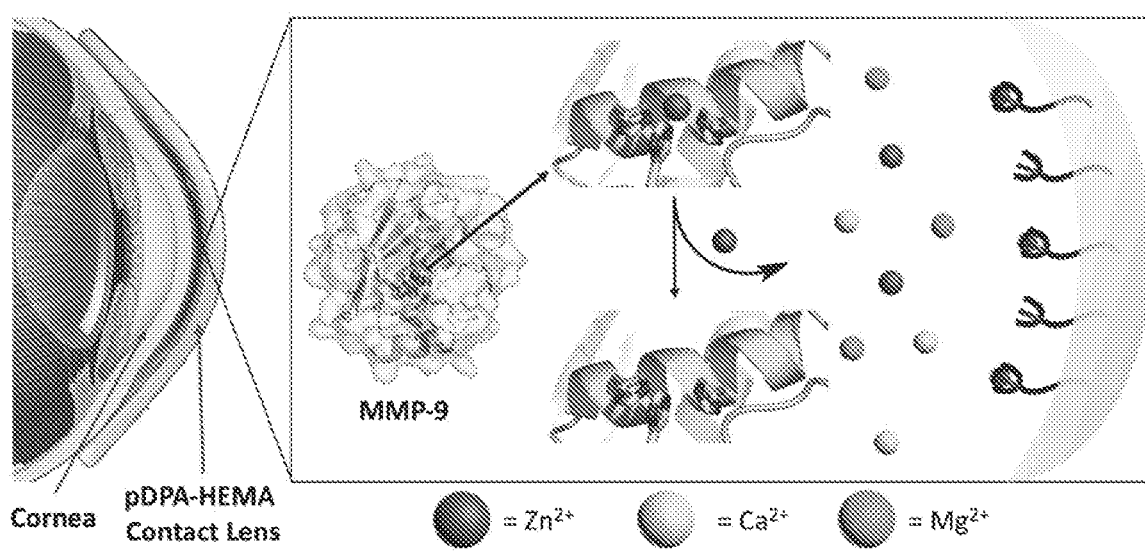

A hydrogel is a crosslinked network of hydrophilic polymers, and due to its high water content, it is an ideal material to interface human tissues. Poly(2-hydroxyethyl methacrylate) (pHEMA) has been widely used as a base material for contact lenses for refractive correction due to its optical clarity, biocompatibility and mechanical stability. Lately, addition of therapeutic capacity to contact lenses for ocular drug delivery and disease diagnosis has been explored. The present invention provides a zinc-absorbing contact lens to treat corneal melting (FIGS. 1A-1B). The hydrogel backbone was made of pHEMA. The pHEMA-based hydrogel contains dipicolylamine (DPA), which has selective binding affinity towards zinc ions through chelation. DPA specifically complexes $Zn^{2+}$ among all divalent cations. The complexation of $Zn^{2+}$ by DPA affords a five-membered chelate ring ($K_d \sim 10^{-11}$ M). DPA does not associate strongly with most metal ions, such as $Ca^{2+}$, $Mg^{2+}$, $Na^+$ and $K^+$, which exist at high concentrations under physiological conditions.

In one aspect, as demonstrated herein, the hydrogels of the invention can be used to deplete the cornea tissue and tear film of zinc ions, leading to the loss of zinc from the MMPs, which are then deactivated. This method is fundamentally different from previous treatments for MMP-associated diseases, in that herein MMPs are deactivated by the absorption of zinc ions instead of the release of therapeutic molecules. This aspect of the treatment substantially reduces the risk of detrimental side effects associated with the circulation and nonspecific actions of therapeutics.

In another aspect, the present invention does not contemplate systemic circulation of zinc-targeting molecules. DPA molecules, which selectively chelate with zinc ions from the tear film, are covalently immobilized in the polymer network of the contact lens. Unlike the currently available MMPi, there is no systemic circulation of zinc-targeting molecules. Therefore, the therapeutic effects and the associated side effects are limited to the affected cornea.

In yet another aspect, DPA is a non-ionic metal chelator, unlike widely used metal ion chelating agents, such as EDTA. This fact is an important aspect of innovation because ionic contact lenses tend to attract charged proteins at the contact lens-cornea interface, which becomes the source of unwanted inflammatory reactions.

In yet another aspect, the present invention further contemplates addition of other metal chelators. The basic platform of the contact lens allows the addition of other chelators that can absorb different metal ions, such as calcium ions. Since MMPs are calcium-dependent as well, absorbing calcium from the tear film can further decrease MMP activities, if necessary.

In yet another aspect, the present invention contemplates drug elution from the contact lens. Controlled release of small molecule drugs from the proposed contact lens can be achieved in order to enhance therapeutic effects. In certain embodiments, a block of drug-containing biodegradable polymers can be incorporated in the contact lens of the invention.

Thus, this novel hydrogel provides an additional treatment to slow down the progression of corneal melting and other ocular diseases.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

Abbreviations used herein include: HEMA=2-hydroxyethyl methacrylate; pHEMA=poly(2-hydroxyethyl methacrylate); DPA=dipicolylamine; MMP=matrix metalloproteinases; EGDMA=ethylene glycol dimethycrylate; pDPA-HEMA=DPA-modified pHEMA.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "abnormal" when used in the context of organisms, tissues, cells or components thereof, refers to those organisms, tissues, cells or components thereof that differ in at least one observable or detectable characteristic (e.g., age, treatment, or time of day) from those organisms, tissues, cells or components thereof that display the "normal" (expected) respective characteristic. Characteristics that are normal or expected for one cell or tissue type might be abnormal for a different cell or tissue type.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, a disease or disorder is "alleviated" if the severity of a symptom of the disease or disorder, the frequency with which such a symptom is experienced by a patient, or both, is reduced.

As used herein, the term "effective amount" or "therapeutically effective amount" of a compound is that amount of compound that is sufficient to provide a beneficial effect to the subject to which the compound is administered.

As used herein, the term "effective amount" of a delivery vehicle refers to an amount sufficient of the delivery vehicle to effectively entrap, bind or deliver a compound.

As used herein, the term "electromagnetic radiation" includes radiation of one or more frequencies encompassed within the electromagnetic spectrum. Non-limiting examples of electromagnetic radiation comprise gamma radiation, X-ray radiation, UV radiation, visible radiation, infrared radiation, microwave radiation, radio waves, and electron beam (e-beam) radiation. In one aspect, electromagnetic radiation comprises ultraviolet radiation (wavelength from about 10 nm to about 400 nm), visible radiation (wavelength from about 400 nm to about 750 nm) or infrared radiation (radiation wavelength from about 750 nm to about 300,000 nm). Ultraviolet or UV light as described herein includes UVA light, which generally has wavelengths between about 320 and about 400 nm, UVB light, which generally has wavelengths between about 290 nm and about 320 nm, and UVC light, which generally has wavelengths between about 200 nm and about 290 nm. UV light may include UVA, UVB, or UVC light alone or in combination with other type of UV light. In one embodiment, the UV light source emits light between about 350 nm and about 400 nm. In some embodiments, the UV light source emits light between about 400 nm and about 500 nm.

As used herein, the term "hydrogel" or "aquagel" refers to a network of oligomers or polymer chains that are water-insoluble, sometimes found as a colloidal gel in which water is the dispersion medium. Hydrogels can generally absorb much fluid and, at equilibrium, typically are composed of 60-90% fluid and only 10-30% polymer. In certain embodiments, the water content of hydrogel is about 70-80%. Hydrogels may be prepared by crosslinking hydrophilic biopolymers or synthetic polymers. Examples of the hydrogels formed from physical or chemical crosslinking of hydrophilic biopolymers include but are not limited to, hyaluronans, chitosans, alginates (including alginate sulfate), collagen, dextran, pectin, carrageenan, polylysine, gelatins or agarose. Examples of hydrogels based on chemical or physical crosslinking synthetic polymers include but are not limited to HEMA, methacrylate-oligolactide-PEO-oligolactide-methacrylate, poly(ethylene glycol) (PEG), poly(propylene glycol) (PPG), PEG-PPG-PEG copolymers (Pluronics), poly(phosphazene), poly(methacrylates), poly (N-vinylpyrrolidone), PL(G)A-PEG-PL(G)A copolymers, or poly(ethylene imine).

As used herein, an "instructional material" includes a publication, a recording, a diagram, or any other medium of expression that can be used to communicate the usefulness of a composition or method of the invention in the kit for treating, preventing or alleviating various diseases or disorders recited herein. Optionally, or alternately, the instructional material can describe one or more methods of treating, preventing or alleviating diseases or disorders in a cell or a tissue of a mammal. The instructional material of the kit of the invention can, for example, be affixed to a container that contains the identified composition or delivery system of the invention or be shipped together with a container that contains the identified composition or delivery system. Alternatively, the instructional material can be shipped separately from the container with the intention that the instructional material and the composition be used cooperatively by the recipient.

As used herein, the terms "patient," "subject," "individual" and the like are used interchangeably, and refer to any animal, or cells thereof whether in vitro or in situ, amenable to the methods described herein. In a non-limiting embodiment, the patient, subject or individual is a human.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "polymerization" or "crosslinking" refers to at least one reaction that consumes at least one functional group in a monomeric molecule (or monomer), oligomeric molecule (or oligomer) or polymeric molecule (or polymer), to create at least one chemical linkage between at least two distinct molecules (e.g., intermolecular bond), at least one chemical linkage within the same molecule (e.g., intramolecular bond), or any combinations thereof. A polymerization or crosslinking reaction may consume between about 0% and about 100% of the at least one functional group available in the system. In one embodiment, polymerization or crosslinking of at least one functional group results in about 100% consumption of the at least one functional group. In other embodiments, polymerization or crosslinking of at least one functional group results in less than about 100% consumption of the at least one functional group.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "therapeutic" treatment refers to a treatment administered to a subject who exhibits signs of pathology, for the purpose of diminishing or eliminating those signs.

As used herein, the term "treating a disease or disorder" means reducing the frequency with which a symptom of the disease or disorder is experienced by a patient. Disease and disorder are used interchangeably herein.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 and the like, as well as individual numbers within that range, for example, 1, 2, 2.7, 3, 4, 5, 5.3, and 6. This applies regardless of the breadth of the range.

Compositions

The invention provides a polymer comprising 2-hydroxyethyl methacrylate (HEMA) monomers and at least one dipicolylamine (DPA)-containing methacrylate monomer.

In certain embodiments, the HEMA monomers are not cross-linked in the polymer, and thus the polymer is linear.

In certain embodiments, the HEMA monomers are at least partially cross-linked in the polymer, and thus the polymer is cross-linked. In other embodiments, the HEMA monomers are at least partially cross-linked by at least one bis-acrylate cross-linking agent. In yet other embodiments, the at least bis-acrylate cross-linking agent is selected from the group consisting of ethylene glycol dimethacrylate, tetraethyleneglycol-dimethacrylate, poly(ethylene glycol) dimethacrylates, the condensation product of bisphenol A and glycidyl methacrylate, 2,2'-bis [4-(3-methacryloxy-2-hydroxypropoxy)-phenyl]propane, hexanediol dimethacrylate, tripropylene glycol dimethacrylate, butanediol dimethacrylate, neopentyl glycol dimethacrylate, diethylene glycol dimethacrylate, triethylene glycol dimethacrylate, dipropylene glycol dimethacrylate, allyl methacrylate trimethylolpropane triacrylate, tricyclodecane dimethanol diacrylate, and any combinations thereof. In yet other embodiments, the at least bis-acrylate cross-linking agent is selected from the group consisting of ethylene glycol dimethycrylate (EGDMA) and poly(ethylene glycol)diacrylate (PEGDA).

The polymers of the invention can be prepared by irradiating a mixture of the HEMA monomers, at least one DPA-containing methacrylate monomer, an acrylate cross-linking agent, and a photo-initiator.

In certain embodiments, the irradiation comprises ultraviolet electromagnetic radiation (wavelength about 10-400 nm), visible electromagnetic radiation (wavelength about 400-750 nm) or infrared electromagnetic radiation (radiation wavelength about 750-300,000 nm). In other embodiments, the electromagnetic radiation comprises ultraviolet or visible electromagnetic radiation.

Ultraviolet or UV light as described herein includes UVA light, which generally has wavelengths between about 320 and about 400 nm, UVB light, which generally has wavelengths between about 290 nm and about 320 nm, and UVC light, which generally has wavelengths between about 200 nm and about 290 nm. UV light may include UVA, UVB, or UVC light alone or in combination with other type of UV light. In certain embodiments, the UV light source emits light between about 350 nm and about 400 nm. In some embodiments, the UV light source emits light between about 400 nm and about 500 nm.

In certain embodiments, the acrylate cross-linking agent is selected from the group consisting of ethylene glycol dimethacrylate, tetraethyleneglycol-dimethacrylate, poly(ethylene glycol) dimethacrylates, the condensation product of bisphenol A and glycidyl methacrylate, 2,2'-bis [4-(3-methacryloxy-2-hydroxypropoxy)-phenyl]propane, hexanediol dimethacrylate, tripropylene glycol dimethacrylate, butanediol dimethacrylate, neopentyl glycol dimethacrylate, diethylene glycol dimethacrylate, triethylene glycol dimethacrylate, dipropylene glycol dimethacrylate, allyl methacrylate trimethylolpropane triacrylate, tricyclodecane dimethanol diacrylate, and combinations thereof.

The photo-initiator contemplated within the invention is a molecule that, upon irradiation with a given wavelength at a given intensity for a given period of time, generates at least one species capable of catalyzing, triggering or inducing a polymerization or crosslinking. A photo-initiator known in the art may be employed, such as a benzoin ether and a phenone derivative such as benzophenone or diethoxyacetophenone.

Non-limiting examples of the photo-initiator contemplated within the invention are: 1-hydroxy-cyclohexyl-phenyl-ketone (IRGACURE® 184; Ciba, Hawthorne, NJ); a 1:1 mixture of 1-hydroxy-cyclohexyl-phenyl-ketone and benzophenone (IRGACURE® 500; Ciba, Hawthorne, NJ); 2-hydroxy-2-methyl-1-phenyl-1-propanone (DAROCUR® 1173; Ciba, Hawthorne, NJ); 2-hydroxy-1-[4-(2-hydroxyethoxy)phenyl]-2-methyl-1-propanone (IRGACURE® 2959; Ciba, Hawthorne, NJ); methyl benzoylformate (DAROCUR® MBF; Ciba, Hawthorne, NJ); oxy-phenyl-acetic acid 2-[2-oxo-2-phenyl-acetoxy-ethoxy]-ethyl ester; oxy-phenyl-acetic 2-[2-hydroxy-ethoxy]-ethyl ester; a mixture of oxy-phenyl-acetic acid 2-[2-oxo-2-phenyl-acetoxy-ethoxy] ethyl ester and oxy-phenyl-acetic 2-[2-hydroxy-ethoxy]-ethyl ester (IRGACURE® 754; Ciba, Hawthorne, NJ); alpha,alpha-dimethoxy-alpha-phenylacetophenone (IRGACURE® 651; Ciba, Hawthorne, NJ); 2-benzyl-2-(dimethylamino)-1-[4-(4-morpholinyl)-phenyl]-1-butanone (IRGACURE® 369; Ciba, Hawthorne, NJ); 2-methyl-1-[4-(methylthio)phenyl]-2-(4-morpholinyl)-1-propanone (IRGACURE® 907; Ciba, Hawthorne, NJ); a 3:7 mixture of 2-benzyl-2-(dimethylamino)-1-[4-(4-morpholinyl) phenyl]-1-butanone and alpha,alpha-dimethoxy-alpha-phenylacetophenone per weight (IRGACURE® 1300; Ciba, Hawthorne, NJ); diphenyl-(2,4,6-trimethylbenzoyl) phosphine oxide (DAROCUR® TPO; Ciba, Hawthorne, NJ); a 1:1 mixture of diphenyl-(2,4,6-trimethylbenzoyl)-phosphine oxide and 2-hydroxy-2-methyl-1-phenyl-1-propanone (DAROCUR® 4265; Ciba, Hawthorne, NJ); phenyl bis(2,4,6-trimethyl benzoyl) phosphine oxide, which may be used in pure form (IRGACURE® 819; Ciba, Hawthorne, NJ) or dispersed in water (45% active, IRGACURE® 819DW; Ciba, Hawthorne, NJ); a 2:8 mixture of phosphine oxide, phenyl bis(2,4,6-trimethyl benzoyl) and 2-hydroxy-2-methyl-1- phenyl-1-propanone (IRGACURE® 2022; Ciba, Hawthorne, NJ); IRGACURE® 2100, which comprises phenyl-bis(2,4,6-trimethylbenzoyl)-phosphine oxide); bis-(eta 5-2, 4-cyclopentadien-1-yl)-bis-[2,6-difluoro-3-(1H-pyrrol-1-yl) phenyl]-titanium (IRGACURE® 784; Ciba, Hawthorne, NJ); (4-methylphenyl) [4-(2-methylpropyl) phenyl]-iodonium hexafluorophosphate (IRGACURE® 250; Ciba, Hawthorne, NJ); 2-(4-methylbenzyl)-2-(dimethylamino)-1-(4-morpholinophenyl)-butan-1-one (IRGACURE® 379; Ciba, Hawthorne, NJ); 4-(2-hydroxyethoxy)phenyl-(2-hydroxy-2-propyl)ketone (IRGACURE® 2959; Ciba, Hawthorne, NJ); bis-(2,6-dimethoxybenzoyl)-2,4,4-trimethylpentylphosphine oxide; a mixture of bis-(2,6-dimethoxybenzoyl)-2,4, 4-trimethylpentylphosphine oxide and 2-hydroxy-2-methyl-1-phenyl-propanone (IRGACURE® 1700; Ciba, Hawthorne, NJ); titanium dioxide; and mixtures thereof.

In certain embodiments, one or more accelerators are utilized in the photopolymerization. Amine accelerators can be used as polymerization accelerators, as well as other accelerators. Polymerization accelerators suitable for use are various organic tertiary amines well known in the art. In visible light curable compositions, the tertiary amines are generally acrylate derivatives such as dimethylaminoethyl methacrylate and, particularly, diethylaminoethyl methacrylate (DEAEMA), EDAB and the like, in an amount of about 0.05 to about 0.5 wt %. The tertiary amines are generally aromatic tertiary amines, such as tertiary aromatic amines such as EDAB, 2-[4-(dimethylamino)phenyl]ethanol, N, N-dimethyl-p-toluidine (commonly abbreviated DMPT), bis (hydroxyethyl)-p-toluidine, triethanolamine, and the like. Such accelerators are generally present at about 0.5 to about 4.0 wt % in the polymeric component. In one embodiment, 0.8 wt % EDAB is used in visible light polymerization.

In certain embodiments, the at least one DPA-containing methacrylate monomer has the formula:

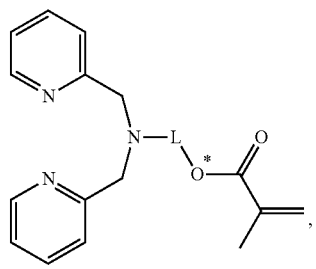

(I)

wherein: L is —(CH$_2$CH$_2$O)$_{m1}$—(CH$_2$CH$_2$)$_{n1}$—X—(CH$_2$CH$_2$O)$_{m2}$—(CH$_2$CH$_2$)$_{n2}$—, wherein the bond marked with  is to the oxygen atom marked with *; m1 is selected from the group consisting of 0, 1, 2, 3, 4, and 5; m2 is selected from the group consisting of 0, 1, 2, 3, 4, and 5; n1 is selected from the group consisting of 0, 1, 2, 3, 4, and 5; n2 is selected from the group consisting of 1, 2, 3, 4, and 5; X is a bond (null) or a pyridylene, wherein if X is pyridylene then m1=n1=1.

In certain embodiments, X is pyridylene and m1=n1=1. In certain embodiments, the pyridylene is 2,6-pyridylene. In certain embodiments, m2=0 and n2=1.

In certain embodiments, the monomer of formula (I) is:

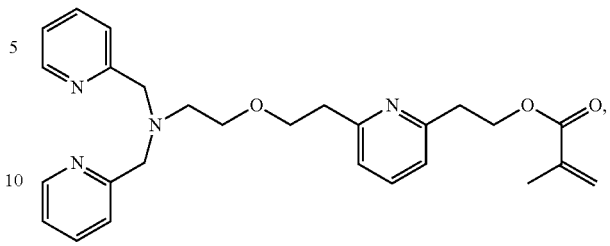

or 2-(6-(2-(2-(bis(pyridin-2-ylmethyl)amino) ethoxy) ethyl)pyridin-2-yl)ethyl methacrylate.

In certain embodiments, the monomer of formula (I) is:

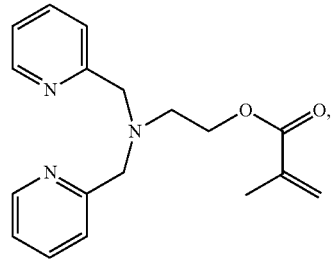 [SMILES: C=C(C)C(=O)OCCN(Cc1ccccn1)Cc1ccccn1]

or 2-(bis(pyridin-2-ylmethyl)amino)ethyl methacrylate.

In certain embodiments, the ratio of the HEMA monomers and at least one DPA-containing methacrylate monomer ranges from about 92:8 to about 99.5:0.5. In other embodiments, the ratio of the HEMA monomers and at least one DPA-containing methacrylate monomer is selected from the group consisting of about 92:8, 92.5:7.5, 93:7, 92.5:7.5, 93:7, 93.5:6.5, 94:6, 94.5:5.5, 95:5, 95.5:4.5, 96:4, 96.5:3.5, 97:3, 97.5:2.5, 98:2, 98.5:1.5, 99:1, and 99.5:0.5.

In certain embodiments, the polymer is a hydrogel. In other embodiments, the polymer is shaped in the form of a contact lens.

In certain embodiments, the at least one DPA-containing methacrylate monomer, or a molecule comprising the DPA, is not significantly released from the polymer.

In certain embodiments, the polymer does not comprise any ionic metal chelator.

Methods

The invention further provides a method of depleting the corneal tissue and/or tear film of an eye of a subject from Zn$^{2+}$ ion. The invention also provides a method of treating keratolysis in an eye of a subject.

In certain embodiments, the method comprises applying to the eye of the subject a contact lens comprising the polymer of the invention. In other embodiments, the eye of the subject suffers from corneal melting or keratolysis. In yet other embodiments, the corneal tissue and/or tear film of the eye of the subject is not substantially depleted from at least one ion selected from Ca$^{2+}$, Mg$^{2+}$, Na$^r$, and K$^+$. In yet other embodiments, the polymer is not substantially cytotoxic to the eye of the subject. In yet other embodiments, the subject does not receive any substantial systemic exposure to DPA from the polymer.

Kit

The invention also provides a kit comprising the polymer of the invention and instructional material for use thereof. In certain embodiments, the instructional material included in the kit comprises instructions for using the polymer of the invention. In certain embodiments, the polymer of the invention is as described elsewhere herein.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Methods and Materials
Materials and Instruments:

Unless specified, chemicals were purchased from Sigma-Aldrich and used without further purification. Zinc assay kit was purchased from Sigma Aldrich, and MMP activity kit was purchased from Abcam, Cambridge, Mass. Pig eyeballs were purchased from VisionTech. Human corneal epithelial cells were purchased from Gibco (ThermoFisher), and human keratocytes were purchased from StemCells. AlamarBlue assay, TUNEL assay, TRITC-labeled phalloidin, and DAPI were purchased from Life Technologies.

Synthesis of DPA-MA:

In order to covalently link DPA into the pHEMA framework, DPA-MA was synthesized by using the procedures detailed herein. The syntheses were confirmed by $^1$H and $^{13}$C NMR spectroscopy, and LC/MS spectrometry.

N,N-bis(2-pyridylmethyl)-2-aminoethanol (DPA-HE):

2-aminoethanol (1.0 g, 16 mmol) and pyridine-2-carbaldehyde (3.5 g, 33 mmol) were dissolved in dry tetrahydrofuran (THF, 100 mL) and then sodium triacetoxyborohydride (14 g, 65 mmol) and glacial acetic acid (2.8 mL, 49 mmol) were added to the solution. The mixture was stirred under a nitrogen atmosphere at room temperature for 3 days. The reaction solution was neutralized with saturated $NaHCO_3$, and then the aqueous solution was extracted with excess dichloromethane. The organic phase was dried over $Na_2SO_4$ and dichloromethane was evaporated under reduced pressure. The crude product was purified by column chromatography on silica gel ($MeOH:CH_2Cl_2$ 10:90) to obtain N,N-bis(2-pyridylmethyl)-2-aminoethanol (DPA-OH) as a pale yellow oil (2.8 g, 12 mmol, 71%). NMR ($CDCl_3$, 300 MHz): δ=2.88 (t, 2H), 3.68 (t, 2H), 3.94 (s, 4H), 7.25 (m, 2H), 7.31 (d, 2H), 7.59 (td, 2H), 8.55 ppm (t, 2H). $^{13}$C NMR ($CDCl_3$, 300 MHz): δ=56.54, 59.40, 60.16, 121.72, 123.06, 136.40, 148.60, 159.08 ppm.

2-(bis(pyridin-2-ylmethyl)amino)ethyl methacrylate (DPA-MA):

Methacryloyl chloride (0.48 mL, 4.9 mmol) was added to a solution of DPA-HE (1.0 g, 4.1 mmol) and triethylamine (0.69 mL, 4.9 mmol) in diethyl ether (30 mL) and the mixture was stirred for 12 h at 0° C. The reaction solution was neutralized with saturated $NaHCO_3$ and then the aqueous solution was extracted with diethyl ether. The organic phase was dried over $Na_2SO_4$ and diethyl ether was evaporated under reduced pressure. The crude product was purified by column chromatography on silica gel ($MeOH:CH_2Cl_2$ 5:95) to obtain 2-(bis(pyridin-2-ylmethyl)amino) ethyl methacrylate (DPA-MA) as a pale yellow oil (1.2 g, 3.9 mmol, 95%). $^1$H NMR ($CDCl_3$, 300 MHz): δ=1.88 (s, 3H), 2.87 (t, 2H), 3.84 (s, 4H), 4.22 (t, 2H), 5.49 (m, 1H), 6.02 (m, 1H), 7.08 (m, 2H), 7.46 (d, 2H), 7.57 (td, 2H), 8.45 ppm (m, 2H). $^{13}$C NMR ($CDCl_3$, 300 MHz): δ=18.23, 52.34, 60.73, 62.45, 121.91, 122.68, 125.35, 136.40, 148.79, 159.46, 159.27 ppm.

Hydrogelation of DPA-Containing pHEMA (pDPA-HEMA):

An aqueous solution was prepared with HEMA and DPA-MA (i.e., 5 and 10% w/v with HEMA), ethylene glycol dimethacrylate (EGDMA) and 0.5 wt % of 2-hydroxy-4'-(2-hydroxyethoxy)-2-methylpropiophenone (photoinitiator Irgacure2959). The solution was stirred for 10-15 mins and then polymerized by UV light (400 W, λmax=365 nm) under nitrogen for 1 hour at room temperature. After polymerization, the hydrogels were washed with distilled water (3 times) to remove the unreacted precursor and residual chemicals.

Optical Property of Hydrogel:

Optical properties of the pDPA-HEMA hydrogel were obtained by forming the hydrogel in 96 well plates and using a microplate reader. Absorbance of 300-700 nm was recorded for both pDPA-HEMA and pHEMA hydrogels.

Zinc Absorption Assay:

A commercially available zinc assay kit (Newport Green DCF) was used to measure the zinc absorbing capacity and selectivity of pDPA-HEMA hydrogels. Circular disc-shaped hydrogels of varying amount of DPA (8.0 mm in diameter and 2.0 mm in thickness) were added in 1 mL phosphate buffered saline (PBS without divalent cations, pH 7.4) at 37° C. supplemented with 1 mM $ZnCl_2$ solution in the presence and absence of 10 mM $CaCl_2$. The solution vials were placed on a shaker. After 1 hour, the concentration of zinc ions was estimated by comparing the fluorescence intensity with that of standard solutions: 1) 100 $\mu$l from the solutions was transferred into a 96-well plate and 100 μL of Newport Green DCF was added into the plate; and fluorescence intensity was measured using a Cytation 3 plate reader (ex 505 nm/em=535 nm).

The number of surface DPA group was estimated by the following order of magnitude analysis. 7.5 μmoles of DPA was uniformly distributed in the full thickness of the hydrogel (2 mm). Since the length of the crosslinker (EGDMA) is in the order of a few nanometers ($10^{-9}$ m), there are approximately mm/nm=~$10^6$ "layers". This means 7.5 μmoles of DPA are dispersed in $10^6$ layers, each layer containing ~μmoles/$10^6$=~pmoles. From this argument, the number of surface DPA is estimated to be in the order of pmoles. To remove 1 μmole of zinc ions, DPA molecules throughout the whole hydrogel volume should participate in the binding event, not just the surface DPA molecules.

TABLE 1

Figure 4A:
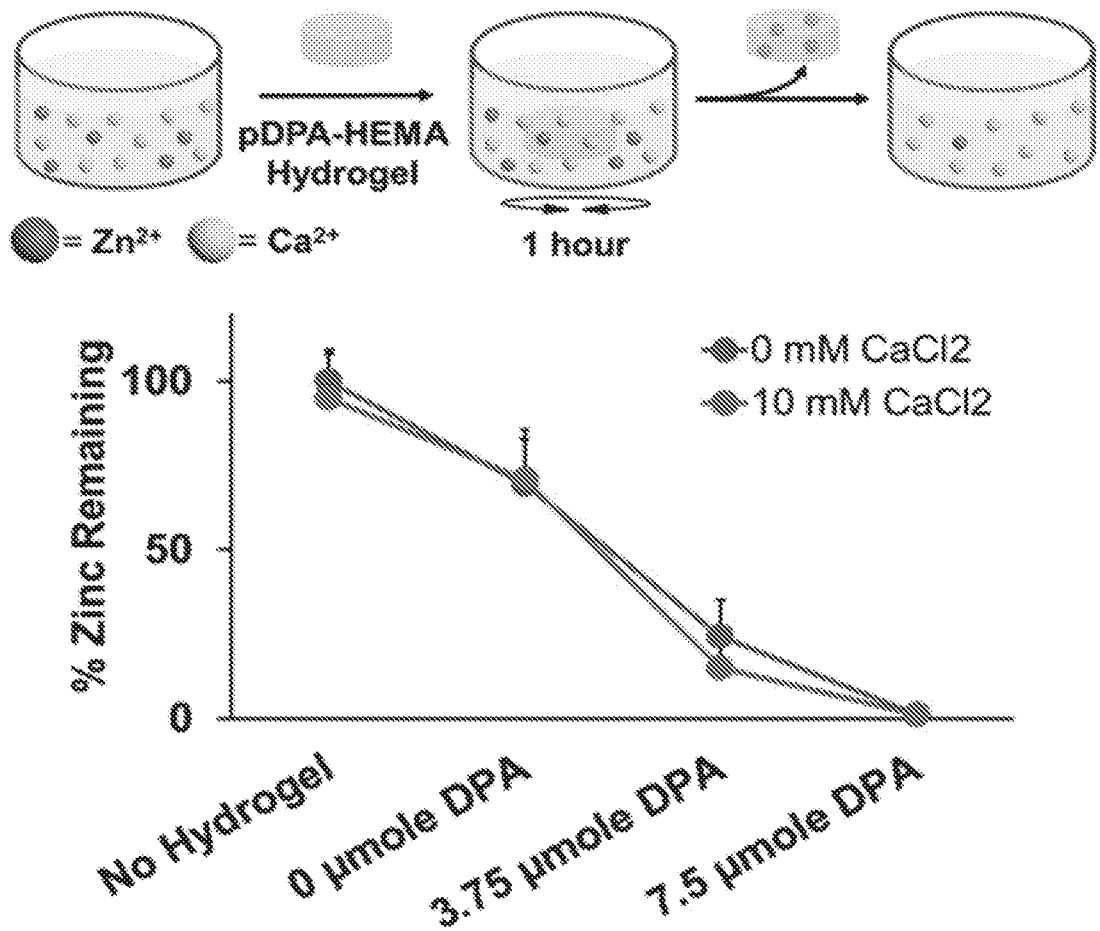
FIGS. 4A-4E illustrate zinc-absorbing capacity of pDPA-HEMA hydrogel.

Partition of zinc ions (1 mM in 1 mL) without calcium ions in the solution based on the results in FIG. 4A. The partition coefficient was calculated by dividing the zinc concentration in the hydrogel by that in the solution. The partition coefficient for 7.5 μmole DPA could not be calculated because the amount of zinc ions in the solution was below the detection limit.

|  | No hydrogel | 0 μmole DPA | 3.75 μmole DPA |
|---|---|---|---|
| [$Zn^{2+}$] in Hydrogel | 0 mM | 0.31 mM | 0.76 mM |
| [$Zn^{2+}$] in Solution | 1 mM | 0.69 mM | 0.24 mM |
| Partition Coefficient | 0 | 0.449 | 3.17 |

TABLE 2

Partition of zinc ions (1 mM in 1mL) with calcium ions (10 mM in 1 mL) in the solution based on the results in FIG. 4A. The partition coefficient was calculated by dividing the zinc concentration in the hydrogel by that in the solution. The partition coefficient for 7.5 μmole DPA could not be calculated because the amount of zinc ions in the solution was below the detection limit.

|  | No hydrogel | 0 μmole DPA | 3.75 μmole DPA |
|---|---|---|---|
| [$Zn^{2+}$] in Hydrogel | 0 mM | 0.29 mM | 0.85 mM |
| [$Zn^{2+}$] in Solution | 1 mM | 0.71 mM | 0.15 mM |
| Partition Coefficient | 0 | 0.408 | 5.67 |

Scanning Electron Microscopy (SEM) and Elemental Analysis:

After the zinc assay, the hydrogels were washed in DI water, frozen at −80° C. and lyophilized. The dried pDPA-HEMA and pHEMA were cut into small pieces, sputter-coated with gold/palladium for SEM (Lyra3 GMU FIB SEM, Tescan, Brno, Czech Republic). Energy dispersive X-ray spectroscopy (EDS) was used in conjunction with SEM to obtain spatial distribution of zinc ions to prove the zinc absorbing capacity of pDPA-HEMA.

MMP Assays:

Prior to measuring MMP activities, 500 μL of MMP-1, MMP-2 or MMP-9 at 1.0 μg/mL was activated by 4-aminophenylmercuric acetate (APMA) for 2 hours at 37° C. During the activation process, a pDPA-HEMA (or pHEMA) hydrogel (8.0 mm in diameter and 2.0 mm thick) was added to the MMP solutions. Enzymatic activity of MMP-1 and MMP-2 by pDPA-HEMA was measured by a commercially available MMP activity kit (Abcam, Cambridge, Mass.). This kit measures the enzymatic activity of a broad spectrum of MMPs by the cleavage of a fluorescently-labeled peptide and Förster Resonance Energy Transfer (FRET). The fluorescence (ex 485 nm/em 520 nm) was measured after 15 and 30 minutes, and the relative MMP activity was calculated by comparing the fluorescence intensity to that of a positive control (MMPs activated with APMA without hydrogels).

Ex Vivo Cornea Degradation:

Porcine cornea tissues were excised from freshly slaughtered pig eyeballs using a biopsy punch (8.0 mm in diameter). The collected cornea tissues were incubated in a collagenase A solution (0.15 or 0.3% w/v in PBS) at 37° C. on a shaker. The corneas were observed macroscopically, and the time that it takes for a cornea to degrade completely was recorded.

Histology:

Cornea tissues were collected from the collagenase A solution before the complete degradation (8 hours), fixed in 4% formaldehyde solution in PBS overnight and stained with hematoxylin and eosin (H&E) for histological analysis.

Biocompatibility:

All in vitro cell culture was performed in a 37° C. humidified incubator with 5% $CO_2$. Human corneal epithelial cells (HCECs) were purchased from Cell Applications (San Diego, Calif.) and cultured in a growth medium containing bovine pituitary extract (BPE). Once the confluent monolayer of epithelial cells is formed, stratification was induced by switching the media to DMEM/F12 supplemented with 10% newborn calf serum, 10 μg/mL epidermal growth factor (EGF) and 1.0% penicillin/streptomycin (pen/strep). The cells were cultured for an additional 48 hours in the presence of pDPA-HEMA and separated by transwell inserts. The proliferation of corneal epithelial cells was measured by alamarBlue assay and was normalized to the proliferation in the absence of pDPA-HEMA.

Human keratocytes were purchased from ScienCells (Carlsbad, Calif.) and cultured in 24 well plates in DMEM supplemented with 10% FBS and 1.0% pen/strep. Once the cells reached the confluence, the hydrogels were added to the culture through the transwell inserts. The proliferation of human keratocytes was monitored over 48 hours by alamarBlue. A TUNEL assay was performed using Click-iT™ TUNEL Alexa Fluor™ 488 Imaging Assay (Thermofisher) to measure the amount of apoptosis during the exposure to the hydrogels.

Statistics

The data is presented in means with standard deviation unless specified otherwise. The statistical significance between the two groups was tested by a student t-test. The multi-sample comparisons were done by ANOVA followed by Tukey post-hoc tests using the statistical tools provided by Origin 8 (Origin, Northampton, Mass.)

Example 1: Synthesis of DPA-Modified Methacrylate (DPA-MA)

Figure 2:
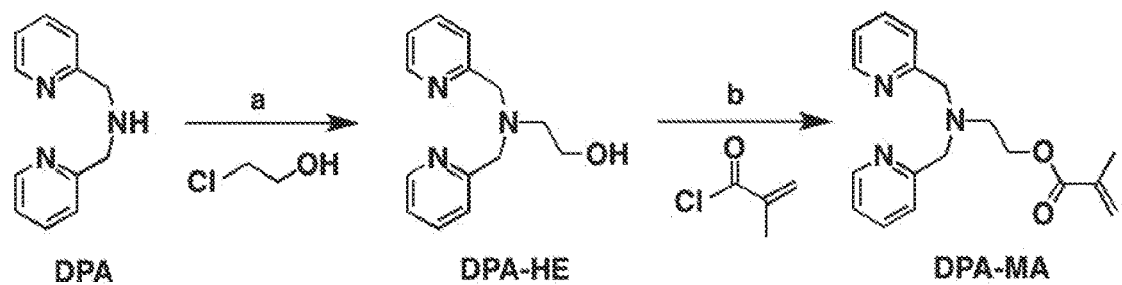
FIG. 2 illustrates examples of syntheses of DPA-MA.
Figure 2:
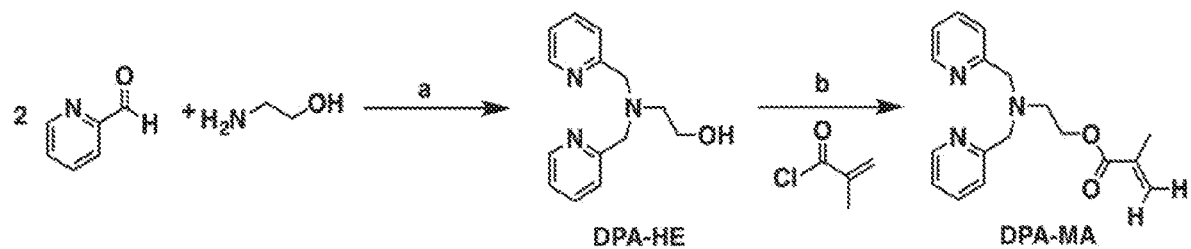

General synthetic strategies were developed for creating therapeutically functional hydrogels. DPA-MA was quantitatively synthesized using a simple two-step synthesis (FIG. 2). DPA-HE was obtained via reductive amination of 2-aminoethanol with pyridine-2-carbaldehyde using a reducing agent, NaBH(AcO)$_3$, and then DPA-HE was reacted with methacryloyl chloride at 0° C. to afford DPA-MA quantitatively.

Example 2: Photo-Polymerization of DPA-Modified pHEMA (pDPA-HEMA)

pDPA-HEMA hydrogel was formed by mixing DPA-MA, HEMA, ethylene glycol dimethacrylate (EGDMA, a crosslinker) and Irgacure 2959 (a photoinitiator) in the presence of water, followed by curing under UV ($\lambda$max=365 nm, 400 W) for 1 h (FIG. 3A). Incorporation of DPA in pHEMA resulted in an optically transparent hydrogel with a slightly yellow tint (FIG. 3B). Although the transmittance of pDPA-HEMA hydrogel was lower than pHEMA hydrogel throughout the entire visible spectrum, it was higher than 0.8 above 436 nm, making it suitable as a contact lens (FIG. 3C).

Example 3: Zinc Absorption Assay

Figures 4B, 4C:
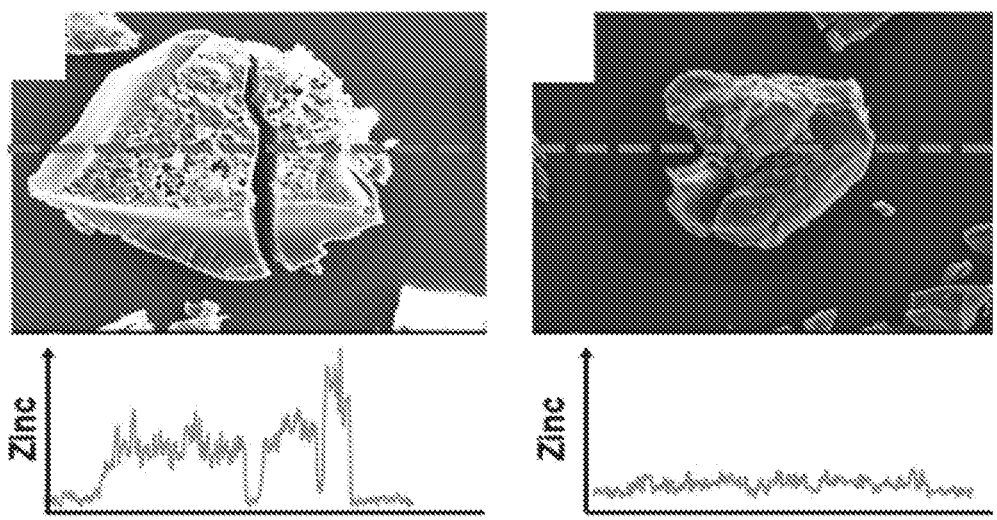
Figure 4D:
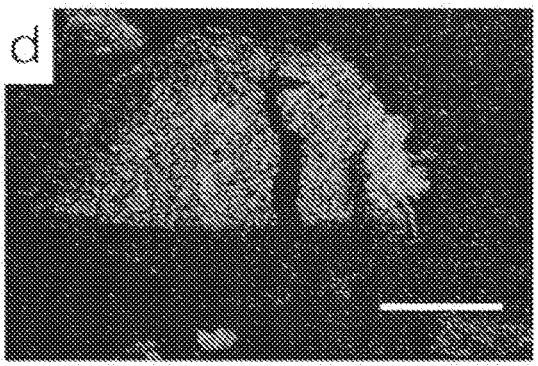
Figure 4E:
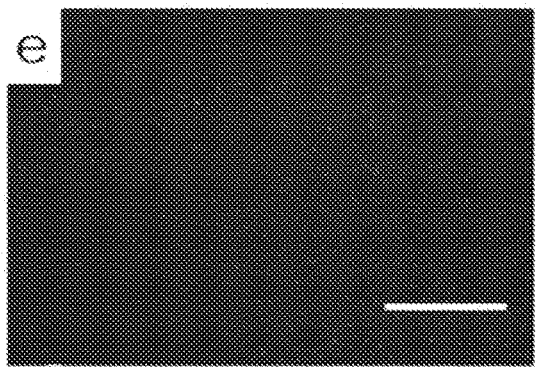

The specific zinc-absorbing capacity of pDPA-HEMA hydrogel is demonstrated herein (FIG. 4A). pDPA-HEMA hydrogels with varying quantities of DPA were incubated in an aqueous zinc solution, and the amount of zinc ions remaining in the solution was measured over different DPA concentrations in the hydrogel. As DPA content increased, more zinc ions were absorbed by the hydrogel. Because the number of DPA on the hydrogel surface was only on the order of picomoles (see the Supporting Information for the detailed order of magnitude analysis) and 1 μmol of zinc ions was removed by the hydrogel, it can be assumed that the binding of zinc ions to DPA occurred not only on the surface but also within the hydrogel. Because of the high selectivity of DPA toward zinc, the zinc-absorbing capacity of pDPA-HEMA hydrogel was unaffected by the presence of calcium at a 10 times higher concentration. pHEMA hydrogel (without DPA) removed a small fraction (30%) of zinc ions, likely due to the weak nonspecific interaction between zinc ions and the hydroxyl groups of pHEMA. However, the amount of removed zinc ions by pHEMA hydrogel was significantly lower than that by pDPA-HEMA hydrogel. FIGS. 4B-4C show scanning electron microscope (SEM) images of small fragments of lyophilized hydrogels after zinc absorption with the elemental analysis performed by energy-dispersive X-ray spectroscopy (EDS). The profile of zinc signal along the dashed-line of the SEM image perfectly matched the profile of the pDPA-HEMA hydrogel (FIG. 4B), indicating that the disappearance of zinc ions from the solution was caused by the accumulation of zinc ions in the pDPA-HEMA hydrogel. No significant amount of zinc was detected on the pHEMA hydrogel (FIG. 4C). When the entire field of the SEM image of the pDPA-HEMA hydrogel was scanned for zinc in the EDS mode, the distribution of zinc was shown to overlap with the zinc in the SEM image (FIG. 4D). A negligible amount of zinc was detected in the pHEMA hydrogel (FIG. 4E). Combined with the zinc assay, these results prove that the inclusion of DPA renders the pHEMA hydrogel with zinc-absorbing capacity.

Example 4: MMP Activity Assay

Figure 5A:
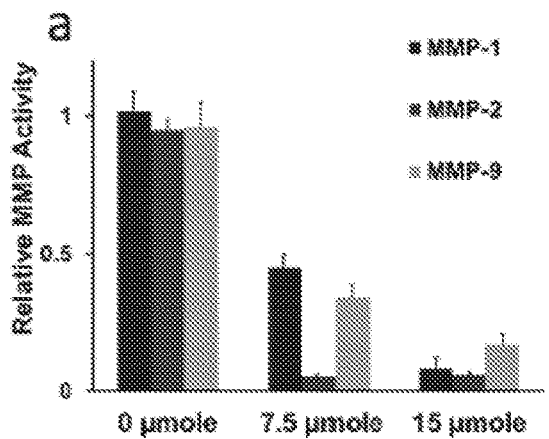
Figure 8:
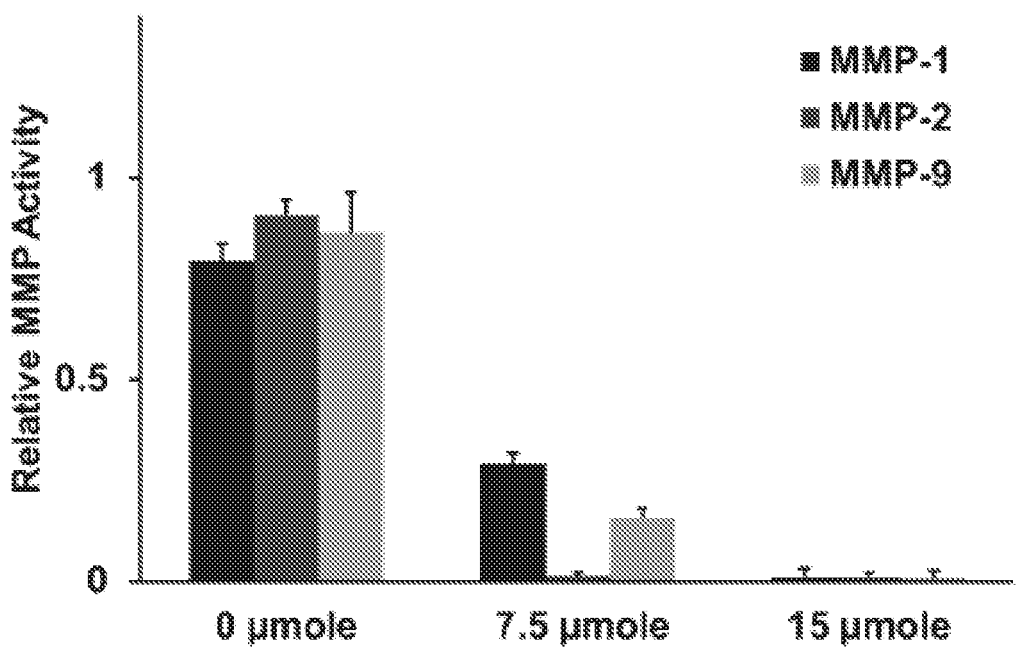
FIG. 8 is a graph illustrating relative MMP activities 15 minutes after the initiation of the assay. Relative MMP activity was measured by normalizing the fluorescence intensity by that of the positive control (MMPs without hydrogels).

Subsequently, it was tested whether removing zinc from the media using pDPA-HEMA hydrogels would lead to the reduction of MMP activities. Interaction between zinc and zinc-binding sites in MMPs is based on the coordination bonds and is reversible with the off-rate of around 3 h; if the surrounding has a low zinc concentration, MMPs eventually lose the zinc ions from the zinc-binding sites and are deactivated. MMP-1, MMP-2, and MMP-9 were chosen as test subjects because they are the major enzymes that are responsible for corneal melting. MMPs were incubated with the hydrogels during the 2 h of MMP activation by 4-aminophenylmercuric acetate (APMA). FIG. 5A and FIG. 8 clearly demonstrate that there is a significant reduction in enzymatic activities of all MMPs that were tested, whereas pHEMA hydrogel (without DPA) had no effects. pDPA-HEMA hydrogel deactivated MMP-2 more effectively than MMP-1 or MMP-9. Because the basic mechanism of MMP deactivation is the loss of zinc ions from the zinc-binding sites of the enzyme, it is expected that this hydrogel can be applied to all other zinc-dependent MMPs, although the effectiveness of deactivation may differ for different MMPs.

Example 5: Ex Vivo Cornea Degradation and Histology

Figure 5B:
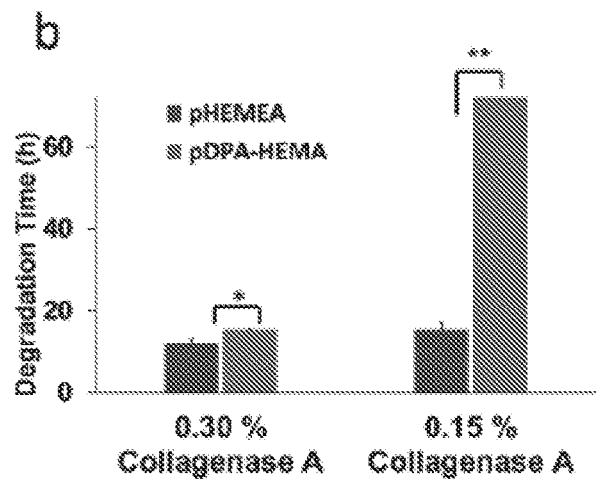

An ex vivo cornea degradation model was used to simulate the corneal melting: (1) porcine corneas have been widely used as a model system for various potential treatments for human corneas; and (2) collagenase A is a zinc-dependent protease, a bacterial analogue of human MMPs, and has been widely used as a model MMP because of its ready availability. When freshly obtained porcine cornea was incubated in 0.3% (w/v) collagenase A solution with pHEMA and pDPA-HEMA hydrogels, the corneas completely degraded within 12 and 15 h, respectively (FIG. 5B). When the collagenase A concentration was reduced to 0.15% (w/v), the degradation time slightly increased to 15 h for pHEMA hydrogel, whereas the corneas did not degrade completely even after 72 h for pDPA-HEMA hydrogel. Corneal melting is a slowly progressing symptom, and the concentration of MMPs in the tear film of the corneal melting patients is in the order of a few nanograms per milliliter, which is orders of magnitude lower than the collagenase A concentrations in the current study. Therefore, it is expected that pDPA-HEMA hydrogels will be highly effective in preventing corneal melting in vivo.

Figure 5C:
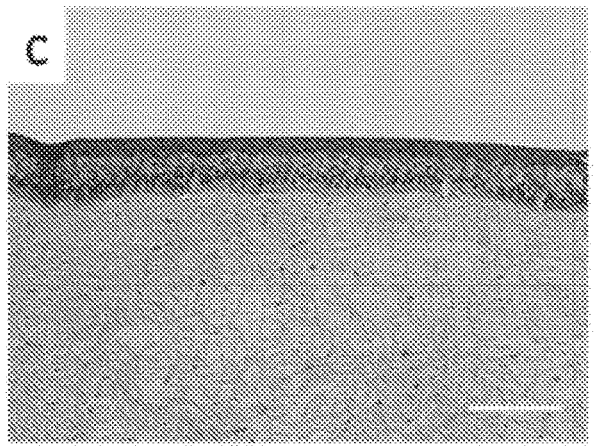
Figure 5D:
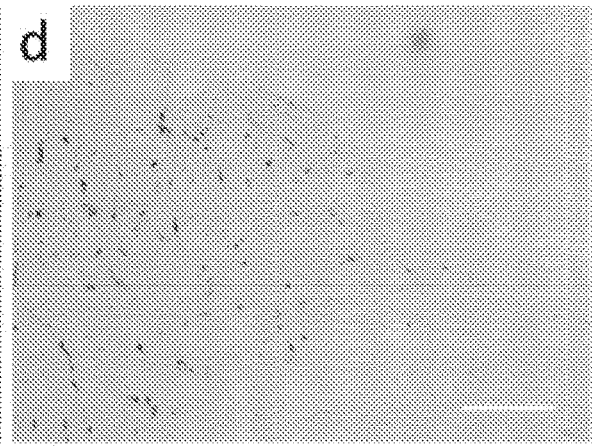
Figure 7:
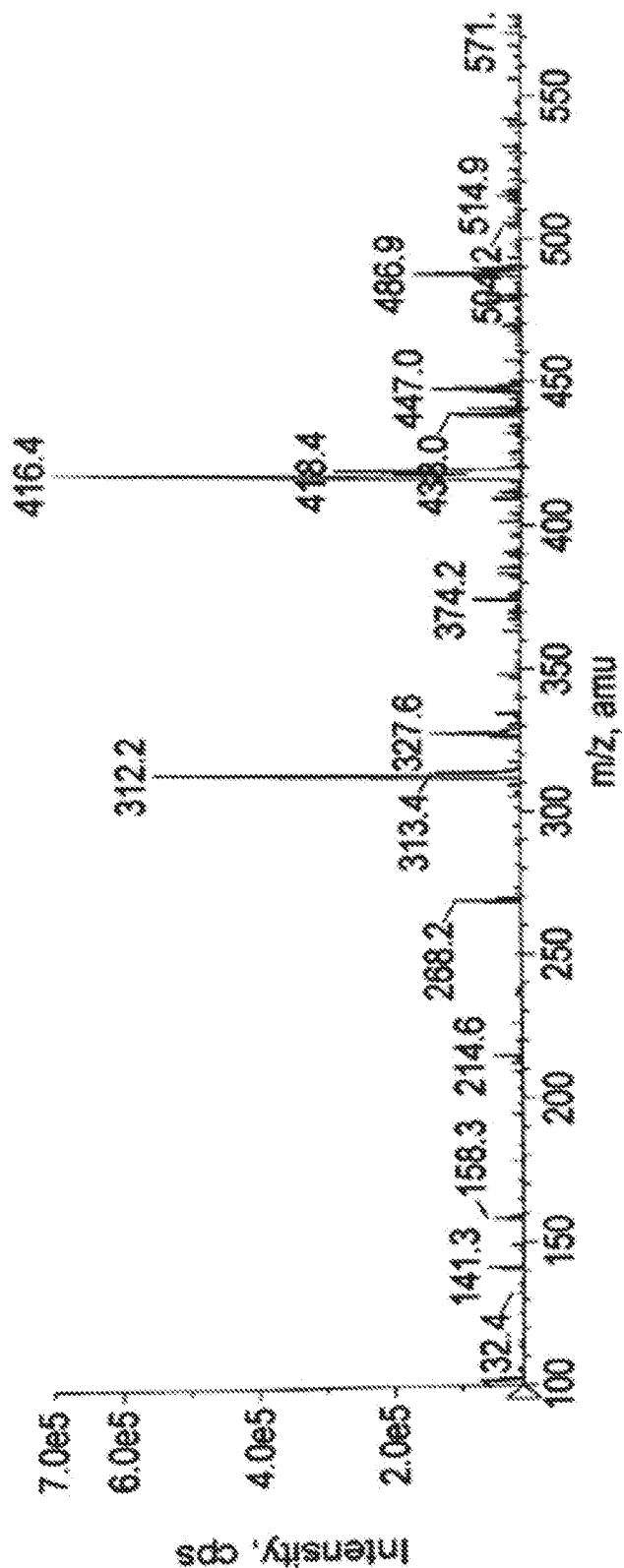
FIG. 7 is a graph showing LC/MS spectrum of DPA-MA (calcd. MW for $[C_{18}H_{21}N_3O_2]^+$ is 311.2 and observed MW for $[M+H]^+$ is 312.2).

To observe the microscopic changes taking place within the degraded cornea tissue, the tissues were fixed before the complete degradation (i.e., 8 h incubation in 0.15% collagenase A solutions). The untreated cornea tissue shows a clear stratified epithelium and a stroma with a well-packed ECM (FIG. 5C). When the cornea was incubated in collagenase A without any hydrogel, the cornea tissue lost the entire epithelium and had many small holes in the exterior of the residual tissue (FIG. 5D). In addition, the H&E staining was much weaker than the untreated cornea tissue, likely due to much degradation of the ECM. The cornea tissue incubated in collagenase A with pHEMA hydrogel had similar structures (FIG. 5E). However, the tissues incubated in collagenase A with pDPA-HEMA hydrogel remained mostly intact except for some damage on the epithelium (FIG. 5F). The results from the cornea degradation study and histological analyses confirm that pDPA-HEMA hydrogel prevents the degradation of corneal ECM by deactivating the collagenase A.

Example 6: Cytotoxicity of pDPA-HEMA

Figure 9B:
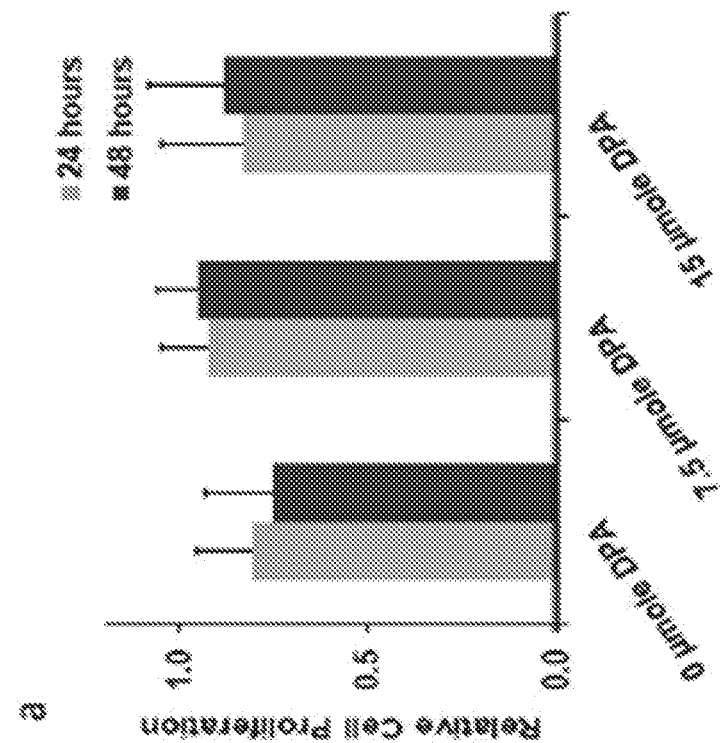
FIGS. 9A-9B are graphs showing proliferation of (FIG. 9A) human corneal epithelial cells (HCECs) (FIG. 9B) human keratocytes in the presence of pHEMA hydrogels. The amount of DPA within the pHEMA hydrogel was changed between 0 and 15 μmoles. The proliferation was normalized to that of the cells with no treatment with hydrogels. No statistically significant differences were observed among all groups at any time. (n=4).
Figure 9A:
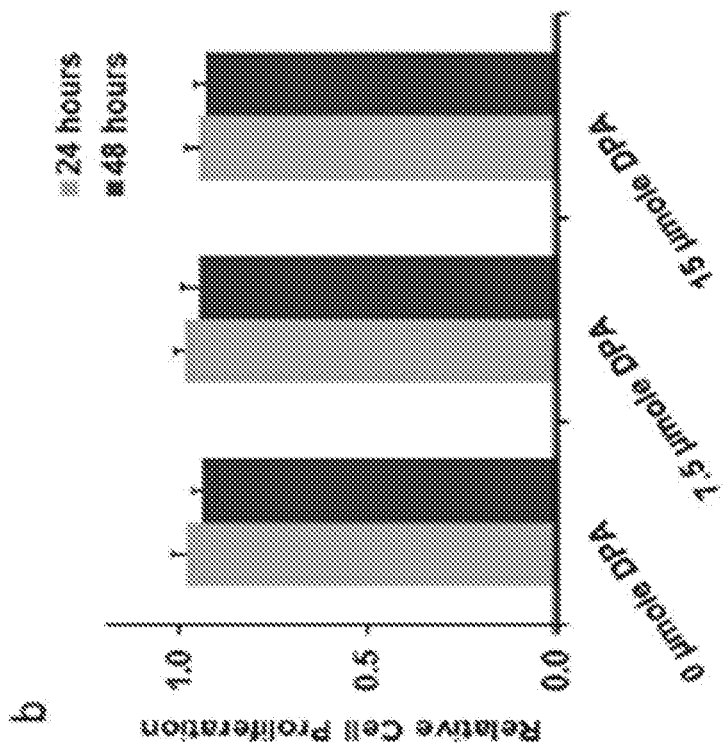
Figure 10:
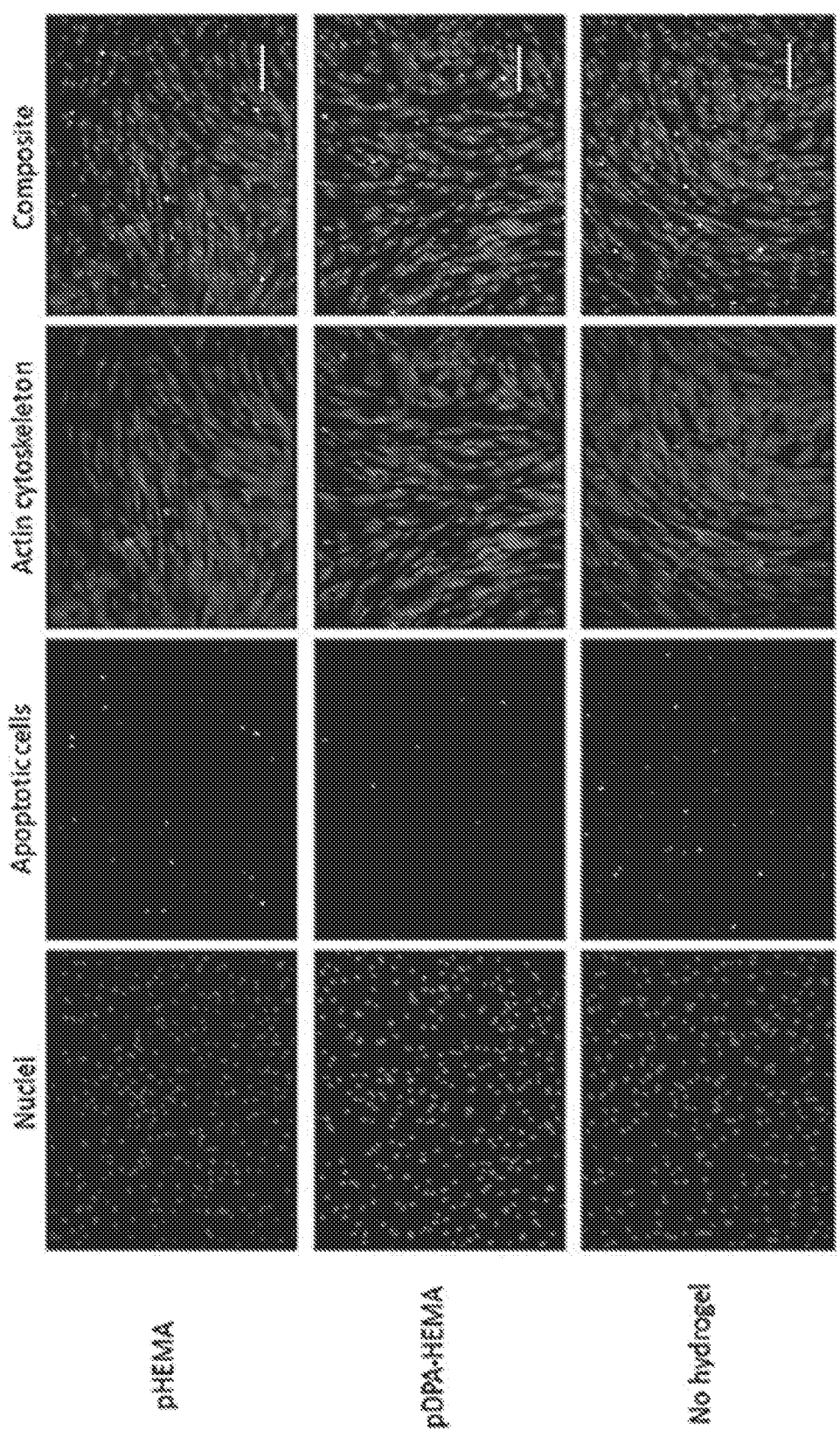
FIG. 10 show representative fluorescence microscope images of TUNEL assay. The nuclei, apoptotic cells and actin cytoskeleton were stained using different colors. (Scale bar=200 μm).
Figure 11:
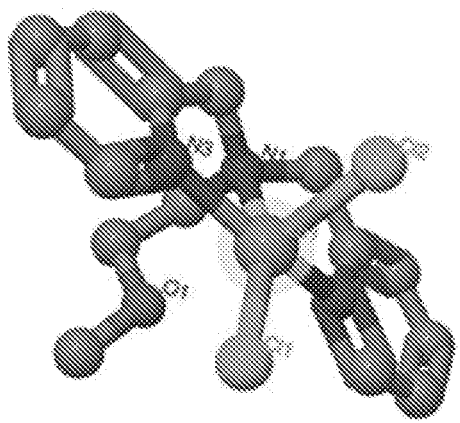
FIG. 11 illustrates a non-limiting DPA-containing monomer useful within the hydrogels of the invention. pDPA-py-HEMA (i.e., an addition of pyridine molecule to DPA) has a tighter association constant to zinc than pDPA-HEMA (by as much as four orders of magnitude) due to the presence of an additional coordination binder (pyridine) for the zinc.
Figure 11:
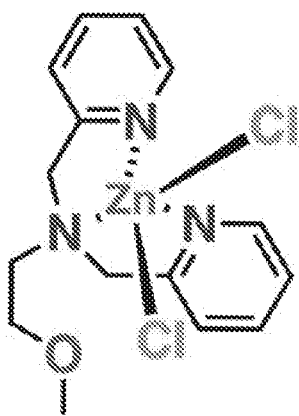
Figure 11:
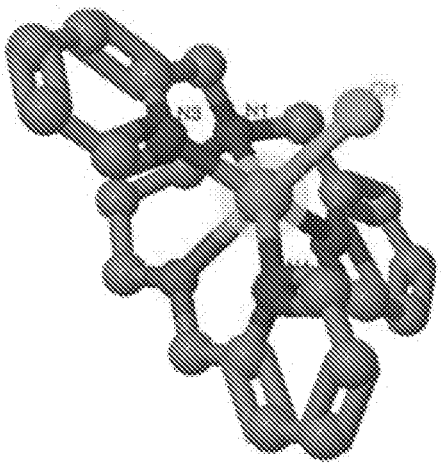
Figure 11:
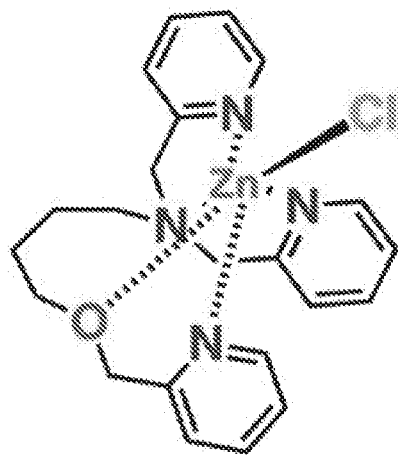
Figure 11:
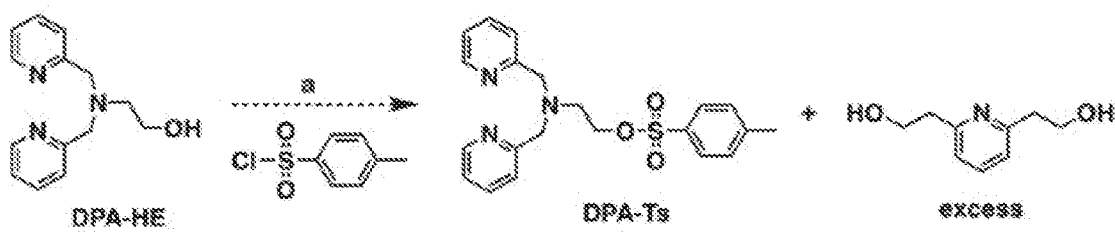
Figure 11:
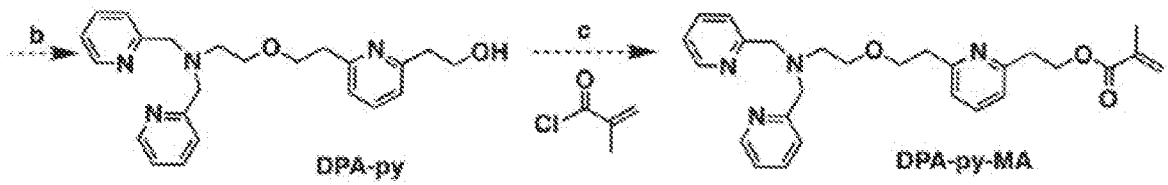

It is important that the removal of zinc ions from the cornea and tear film does not cause cytotoxicity. Cytotoxicity was tested on human corneal epithelial cells (HCECs) and human keratocytes because these cells are most likely to be impacted by the alterations in zinc concentration by the hydrogels. The cells were cultured in 24-well tissue culture plates and were exposed to the hydrogels through semipermeable membranes. For both HCECs and human keratocytes, no significant cytotoxicity by pDPA-HEMA hydrogels was observed for 48 h (FIGS. 9A-9B). Relatively early time points (24 and 48 h) were chosen for the cytotoxicity tests because the contact lenses in general are not worn for an extended period. The pDPA-HEMA hydrogel did not cause any significant level of apoptosis either (FIG. 10).

Example 7

The potential treatment using the pDPA-HEMA contact lens for corneal melting is more advantageous compared to the conventional treatments for the following reasons: (1) Unlike the currently available MMPi, there is no systemic circulation of the zinc-targeting molecules because the DPA molecules are covalently conjugated in the polymer network of the contact lens; thus, the therapeutic effects and the associated side effects are limited to the affected cornea; and (2) DPA selectively binds to a zinc ion among all (biological) metal ions, which further decreases the chance of side effects resulting from the depletion of other metal ions.

pDPA-HEMA hydrogels can be synthesized on a large scale at a low cost, and can be treated by the same standard sterilization techniques as pHEMA hydrogels, which ensures the practicality of this material.

In conclusion, pDPA-HEMA hydrogel was able to deactivate MMPs by selectively removing zinc ions. The results presented herein suggest that the pDPA-HEMA hydrogel can be a useful therapeutic option for treating corneal melting.

ENUMERATED EMBODIMENTS

The following exemplary embodiments are provided, the numbering of which is not to be construed as designating levels of importance:

Embodiment 1 provides a polymer comprising 2-hydroxyethyl methacrylate (HEMA) monomers and at least one dipicolylamine (DPA)-containing methacrylate monomer.

Embodiment 2 provides the polymer of embodiment 1, wherein the HEMA monomers are at least partially cross-linked.

Embodiment 3 provides the polymer of any one of embodiments 1-2, wherein the HEMA monomers are at least partially cross-linked by at least one bis-acrylate cross-linking agent.

Embodiment 4 provides the polymer of any one of embodiments 1-3, wherein the at least bis-acrylate cross-linking agent is selected from the group consisting of ethylene glycol dimethacrylate, tetraethyleneglycol-dimethacrylate, poly(ethylene glycol) dimethacrylates, the condensation product of bisphenol A and glycidyl methacrylate, 2,2'-bis [4-(3-methacryloxy-2-hydroxypropoxy)-phenyl] propane, hexanediol dimethacrylate, tripropylene glycol dimethacrylate, butanediol dimethacrylate, neopentyl glycol dimethacrylate, diethylene glycol dimethacrylate, triethylene glycol dimethacrylate, dipropylene glycol dimethacrylate, allyl methacrylate trimethylolpropane triacrylate, tricyclodecane dimethanol diacrylate, and any combinations thereof.

Embodiment 5 provides the polymer of any one of embodiments 1-4, wherein the at least bis-acrylate cross-linking agent is selected from the group consisting of ethylene glycol dimethycrylate (EGDMA), and poly(ethylene glycol) diacrylate (PEGDA).

Embodiment 6 provides the polymer of embodiments 1-5, wherein the at least one DPA-containing methacrylate monomer has the formula:

(I)

wherein: L is $-(CH_2CH_2O)_{m1}-(CH_2CH_2)_{n1}-X-(CH_2CH_2O)_{m2}-(CH_2CH_2)_{n2}-$, wherein the bond marked with  is to the oxygen atom marked with *; m1 is selected from the group consisting of 0, 1, 2, 3, 4, and 5; m2 is selected from the group consisting of 0, 1, 2, 3, 4, and 5; n1 is selected from the group consisting of 0, 1, 2, 3, 4, and 5; n2 is selected from the group consisting of 1, 2, 3, 4, and 5; X is a bond (null) or a pyridylene, wherein if X is pyridylene then m1=n1=1.

Embodiment 7 provides the polymer of any one of embodiments 1-6, wherein X is pyridylene and m1=n1=1.

Embodiment 8 provides the polymer of any one of embodiments 1-7, wherein the pyridylene is 2,6-pyridylene.

Embodiment 9 provides the polymer of any one of embodiments 1-8, wherein m2=0 and n2=1.

Embodiment 10 provides the polymer of any one of embodiments 1-9, wherein the monomer of formula (I) is:

or 2-(6-(2-(2-(bis(pyridin-2-ylmethyl)amino)ethoxy)ethyl) pyridin-2-yl)ethyl methacrylate.

Embodiment 11 provides the polymer of embodiments 1-10, wherein the monomer of formula (I) is:

or 2-(bis(pyridin-2-ylmethyl)amino)ethyl methacrylate.

Embodiment 12 provides the polymer of any one of embodiments 1-11, wherein the ratio of the HEMA monomers and at least one DPA-containing methacrylate monomer ranges from about 92:8 to about 99.5:0.5.

Embodiment 13 provides the polymer of any one of embodiments 1-12, wherein the polymer is a hydrogel.

Embodiment 14 provides the polymer of any one of embodiments 1-13, which is shaped in the form of a contact lens.

Embodiment 15 provides the polymer of any one of embodiments 1-14, wherein the at least one DPA-containing methacrylate monomer, or a molecule comprising DPA, is not significantly released from the polymer.

Embodiment 16 provides the polymer of any one of embodiments 1-15, which does not comprise any ionic metal chelator.

Embodiment 17 provides a method of depleting the corneal tissue and/or tear film of an eye of a subject from $Zn^{2+}$ ion, the method comprising applying to the eye of the subject a contact lens comprising the polymer of any one of embodiments 1-16.

Embodiment 18 provides the method of embodiment 17, wherein the eye of the subject suffers from corneal melting or keratolysis.

Embodiment 19 provides the method of any one of embodiments 17-18, wherein the corneal tissue and/or tear film of the eye of the subject is not substantially depleted from at least one ion selected from $Ca^{2+}$, $Mg^{2+}$, $Na^r$, and $K^+$.

Embodiment 20 provides the method of any one of embodiments 17-19, wherein the polymer is not substantially cytotoxic to the eye of the subject.

Embodiment 21 provides the method of any one of embodiments 17-20, wherein the subject does not receive any substantial systemic exposure to DPA from the polymer.

Embodiment 22 provides a method of treating keratolysis in an eye of a subject, the method comprising applying to the eye of the subject a contact lens comprising the polymer of any one of embodiments 1-16.

Embodiment 23 provides a method of embodiment 22, wherein the polymer is not substantially cytotoxic to the eye of the subject.

Embodiment 24 provides a method of any one of embodiments 22-23, wherein the subject does not receive any substantial systemic exposure to DPA from the polymer.

Embodiment 25 provides a kit comprising the polymer of any one of embodiments 1-16 and instructional material for use thereof, wherein the instructional material includes instructions for using the polymer of the invention.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A polymer comprising 2-hydroxyethyl methacrylate (HEMA) monomers and at least one dipicolylamine (DPA)-containing methacrylate monomer, wherein the HEMA monomers are at least partially cross-linked.

2. The polymer of claim 1, wherein the HEMA monomers are at least partially cross-linked by at least one bis-acrylate cross-linking agent.

3. The polymer of claim 2, wherein the at least one bis-acrylate cross-linking agent is selected from the group consisting of ethylene glycol dimethacrylate, tetraethyleneglycol-dimethacrylate, poly(ethylene glycol) dimethacrylates, the condensation product of bisphenol A and glycidyl methacrylate, 2,2'-bis [4-(3-methacryloxy-2-hydroxypropoxy)-phenyl]propane, hexanediol dimethacrylate, tripropylene glycol dimethacrylate, butanediol dimethacrylate, neopentyl glycol dimethacrylate, diethylene glycol dimethacrylate, triethylene glycol dimethacrylate, dipropylene glycol dimethacrylate, allyl methacrylate trimethylolpropane triacrylate, tricyclodecane dimethanol diacrylate, and any combinations thereof.

4. The polymer of claim 2, wherein the at least one bis-acrylate cross-linking agent is selected from the group consisting of ethylene glycol dimethycrylate (EGDMA) and poly(ethylene glycol) diacrylate (PEGDA).

5. The polymer of claim 1, wherein the at least one DPA-containing methacrylate monomer has the formula:

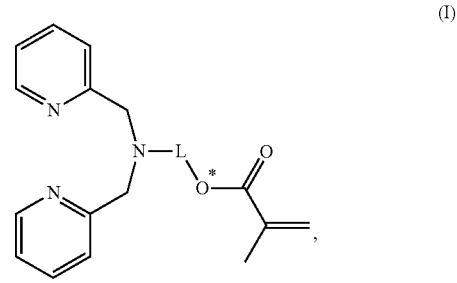

(I)

wherein:
L is $-(CH_2CH_2O)_{m1}-(CH_2CH_2)_{n1}-X-(CH_2CH_2O)_{m2}-(CH_2CH_2)_{n2}-$, wherein the bond marked with  is to the oxygen atom marked with *;
m1 is selected from the group consisting of 0, 1, 2, 3, 4, and 5;
m2 is selected from the group consisting of 0, 1, 2, 3, 4, and 5;
n1 is selected from the group consisting of 0, 1, 2, 3, 4, and 5;
n2 is selected from the group consisting of 1, 2, 3, 4, and 5;
X is a bond or a pyridylene,
wherein if X is pyridylene then m1=n1=1.

6. The polymer of claim 5, wherein X is 2,6-pyridylene.

7. The polymer of claim 5, wherein m2=0 and n2=1.

8. The polymer of claim 5, wherein the monomer of formula (I) is:

(a)

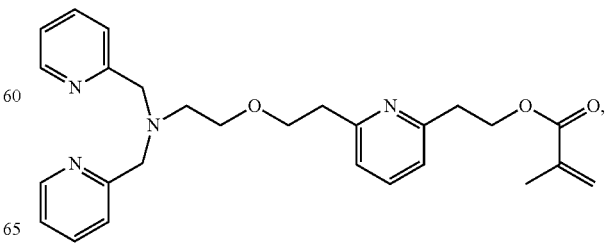

2-(6-(2-(2-(bis(pyridin-2-ylmethyl)amino)ethoxy)ethyl)pyridin-2-yl)ethyl methacrylate; or (b)

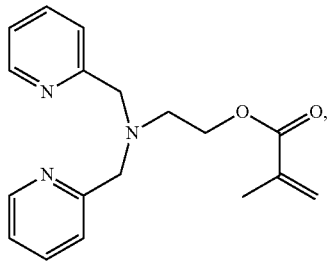 [SMILES: C=C(C)C(=O)OCCN(Cc1ccccn1)Cc1ccccn1]

2-(bis(pyridin-2-ylmethyl)amino)ethyl methacrylate.

9. The polymer of claim 1, which is at least one of:
(a) a hydrogel; and
(b) shaped in the form of a contact lens.

10. The polymer of claim 1, which does not comprise any ionic metal chelator.

11. A method of depleting a corneal tissue or tear film of an eye of a subject of $Zn^{2+}$ ions, the method comprising applying to the eye of the subject a contact lens comprising the polymer of claim 1.

12. The method of claim 11, wherein the eye of the subject suffers from corneal melting or keratolysis.

13. The method of claim 11, wherein the corneal tissue or tear film of the eye of the subject is not substantially depleted of at least one ion selected from $Ca^{2+}$, $Mg^{2+}$, $Na^+$, and $K^+$.

14. The method of claim 11, wherein the polymer is not at least one of:
(a) substantially cytotoxic to the eye of the subject; and
(b) a substantial source of systemic DPA exposure to the subject.

15. A method of treating keratolysis in an eye of a subject, the method comprising applying to the eye of the subject a contact lens comprising the polymer of claim 1.

16. The method of claim 15, wherein the polymer is not at least one of:
(a) substantially cytotoxic to the eye of the subject; and
(b) a substantial source of systemic DPA exposure to the subject.

17. A kit comprising the polymer of claim 1 and instructional material for use thereof, wherein the instructional material includes instructions for using the polymer of claim 1.

* * * * *